(12) United States Patent
Kreichauf et al.

(10) Patent No.: US 6,701,772 B2
(45) Date of Patent: Mar. 9, 2004

(54) CHEMICAL OR BIOLOGICAL ATTACK DETECTION AND MITIGATION SYSTEM

(75) Inventors: Ruth D. Kreichauf, River Falls, WI (US); Keith L. Curtner, St. Paul, MI (US)

(73) Assignee: Honeywell International Inc., Morristown, NJ (US)

(*) Notice: Subject to any disclaimer, the term of this patent is extended or adjusted under 35 U.S.C. 154(b) by 0 days.

(21) Appl. No.: 09/746,688

(22) Filed: Dec. 22, 2000

(65) Prior Publication Data

US 2002/0078771 A1 Jun. 27, 2002

(51) Int. Cl.[7] .......................... B25J 19/02; B25J 19/04; G01N 33/22; G01N 33/497
(52) U.S. Cl. ................... 73/23.2; 73/23.31; 73/31.02; 73/31.03; 73/865.8; 73/866.5; 82/118; 82/158; 901/1; 901/46; 901/47
(58) Field of Search ................... 73/23.2, 31.01, 73/31.02, 31.03, 866.5, 865.8, 23.31; 348/82, 118, 158, 211.2; 701/2; 901/1, 46, 47

(56) References Cited

U.S. PATENT DOCUMENTS

| | | |
|---|---|---|
| 2,598,207 A | 5/1952 | Bailey et al. |
| 3,129,765 A | 4/1964 | Wait |
| 3,592,207 A | 7/1971 | Borello |
| 3,713,491 A | 1/1973 | Grabowski et al. |
| 3,715,131 A | 2/1973 | Hurley et al. |
| 3,730,998 A | 5/1973 | Schmidt et al. |
| 3,741,585 A | 6/1973 | Hendrickson et al. |
| 3,863,720 A | 2/1975 | Young |
| 3,904,221 A | 9/1975 | Shiki et al. |
| 3,920,803 A | 11/1975 | Boryta |
| 3,985,076 A | 10/1976 | Schneiter et al. |
| 4,005,876 A | 2/1977 | Jorgensen et al. |
| 4,020,477 A | 4/1977 | Holland |

(List continued on next page.)

FOREIGN PATENT DOCUMENTS

| | | |
|---|---|---|
| FR | 2 770 781 A | 5/1999 |
| GB | 2 121 950 A | 1/1984 |
| GB | 2 137 389 A | 10/1984 |
| JP | 406 000 230 | 1/1994 |

OTHER PUBLICATIONS

Dorcas Co., Ltd., Home Page, Dr. Oxygen, 6 sheets, dated Jun. 22, 1999 at dr-oxygen.com.

World Trade Search Listing for Hoshiko, Inc. and Hoshiko, Inc, web site for Genox, 5 sheets, dated Jun. 22, 1999 at hoshiko.com.

Judith Anne Yeaple, "Robot Insects", *Popular Science*, Mar. 1991, vol. 238, No. 3, pp. 52–55.

Jerome Greer Chandler, "Micro Planes", *Popular Science*, Jan. 1998, pp. 54–59.

Author unknown, *Popular Science*, Sep. 1999, 2 pages copied onto one sheet.

(List continued on next page.)

*Primary Examiner*—Daniel S. Larkin
(74) *Attorney, Agent, or Firm*—Kris T. Fredrick

(57) ABSTRACT

Systems and methods for monitoring buildings to detect harmful chemical or biological agents. Self-propelled harmful agent detectors are provided that can propel themselves using motors and self-contained power sources. On-board harmful agent sensors can detect the presence of harmful agents and transmit information for reception by a receiving unit. Some sensors can identify the type of agent and transmit the agent type. Some detectors can measure the intensity or concentration of the harmful agent presence and transmit that intensity. Some systems include locating devices for determining positions of the roaming detectors, as well as mapping software to map the location of the individual moving detectors. Systems may include software for plotting the relative concentrations of agents detected to locate the origination of the source within the building. The moving detectors can have motors coupled to wheels, tracks, capstans, pulleys and winches to move the devices along floors, air ducts, and suspended or hanging wires.

39 Claims, 5 Drawing Sheets

U.S. PATENT DOCUMENTS

| | | | |
|---|---|---|---|
| 4,095,211 A | | 6/1978 | Shaughnessy |
| 4,096,639 A | | 6/1978 | Sandrock |
| 4,232,184 A | | 11/1980 | Faust |
| 4,232,308 A | | 11/1980 | Lee et al. |
| 4,238,464 A | | 12/1980 | Gustafson |
| 4,294,420 A | | 10/1981 | Broquet |
| 4,315,361 A | | 2/1982 | Brooks |
| 4,359,097 A | | 11/1982 | Claussen |
| 4,380,187 A | | 4/1983 | Wicks |
| 4,409,978 A | | 10/1983 | Bartos |
| 4,490,272 A | | 12/1984 | Malafosse et al. |
| 4,508,700 A | | 4/1985 | Hoshiko |
| 4,511,887 A | | 4/1985 | Fiore |
| 4,519,177 A | | 5/1985 | Russell |
| 4,522,116 A | | 6/1985 | Tartaglino |
| 4,523,184 A | | 6/1985 | Abel |
| 4,530,744 A | | 7/1985 | Smith |
| 4,575,712 A | | 3/1986 | Winick |
| 4,631,872 A | | 12/1986 | Daroga |
| 4,662,269 A | | 5/1987 | Tartaglino |
| 4,709,265 A | * | 11/1987 | Silverman et al. ............ 73/863 |
| 4,742,956 A | | 5/1988 | Zelczer |
| 4,774,939 A | | 10/1988 | Disney |
| 4,783,045 A | | 11/1988 | Tartaglino |
| 4,817,828 A | | 4/1989 | Goetz |
| 4,877,506 A | | 10/1989 | Fee et al. |
| 4,893,113 A | | 1/1990 | Park et al. |
| 4,901,715 A | | 2/1990 | Mulcahy |
| 4,991,658 A | | 2/1991 | Shlomo |
| 5,074,137 A | | 12/1991 | Harris et al. |
| 5,113,854 A | | 5/1992 | Dosch et al. |
| 5,210,985 A | | 5/1993 | Hsu |
| 5,234,374 A | | 8/1993 | Hyzyk et al. |
| 5,253,901 A | | 10/1993 | Hunter |
| 5,338,516 A | | 8/1994 | Zhang et al. |
| 5,348,270 A | | 9/1994 | Dinh |
| 5,350,033 A | * | 9/1994 | Kraft ......................... 180/167 |
| 5,353,879 A | | 10/1994 | Watanabe et al. |
| 5,370,147 A | | 12/1994 | Brusse et al. |
| 5,399,121 A | | 3/1995 | Gray et al. |
| 5,443,354 A | | 8/1995 | Stone et al. |
| 5,449,112 A | | 9/1995 | Heitman et al. |
| 5,452,639 A | | 9/1995 | Aulenbacher et al. |
| 5,570,477 A | | 11/1996 | Rodriguez |
| 5,617,922 A | | 4/1997 | Sundholm |
| 5,626,151 A | | 5/1997 | Linden |
| 5,648,914 A | | 7/1997 | Bauer et al. |
| 5,660,212 A | | 8/1997 | Elder |
| 5,720,659 A | | 2/1998 | Wicks |
| 5,741,014 A | | 4/1998 | Wambeke et al. |
| 5,761,206 A | | 6/1998 | Kackman |
| 5,808,541 A | | 9/1998 | Golden |
| 5,809,013 A | | 9/1998 | Kackman |
| 5,828,300 A | | 10/1998 | Addy et al. |
| 5,855,510 A | | 1/1999 | McKenzie |
| 5,874,046 A | | 2/1999 | Megerle |
| 5,906,238 A | | 5/1999 | Carmody et al. |
| 5,947,207 A | | 9/1999 | Conforti et al. |
| 5,979,565 A | | 11/1999 | Wicks et al. |
| 5,989,824 A | | 11/1999 | Birmingham et al. |
| 6,010,554 A | | 1/2000 | Birmingham et al. |
| 6,062,392 A | | 5/2000 | Birmingham et al. |
| 6,084,510 A | * | 7/2000 | Lemelson et al. .......... 340/539 |
| 6,217,441 B1 | | 4/2001 | Pearman et al. |
| 6,293,861 B1 | | 9/2001 | Berry |
| 6,296,693 B1 | | 10/2001 | McCarthy |

OTHER PUBLICATIONS

Author Unknown, *Popular Science*, Dec. 1998, p. 63.

Kawai, N. and Janni, J., "Chemical Identification with a Portable Raman Analyzer and Forensic Spectral Database," Spectroscopy vol. 15, Oct. 10, 2000, pp. 33–41.

Krafthefer, B.C., Streifel, A.J., Bridges, and B.B., Grimsrud, "Pressure Relationships in Hospital Critical–Care Facilities," University of Minnesota, USA; Honeywell, Inc. USA.

Chemical and Biological Defense Program Annual Report to Congress, Department of Defense, Mar., 2000.

Birmingham, J. and Hammerstrom, D., "Bacterial Decontamination Using Ambient Pressure Nonthermal Discharges," IEEE vol. 28, 1, pp. 51–55, Feb. 2000.

J. Birmingham, P. Demirev, Y. Ho, J. Thomas, W. Bryden, and C. Fenselau, "Corona Plasma Discharge for Rapid Analysis of Microorganisms by Mass Spectroscopy," Rapid Communications in Mass Spectrometry, 13, pp. 604–606, 1999.

CONPLAN United States Government Interagency Domestic Terrorism Concept of Operations Plan, Jan. 2001.

Sidell, F. R. M.D. et al., Medical Aspects of Chemical and Biological Warfare, Office of the Surgeon General at TMM Publications, 1977.

Curtner, K. L. et al., "Simulation–Based Features of the Compressed Air System Description Tool 'XCEED™'", pp. 1–6.

Burch, S. M., PE, et al., "Chapter 8: Economic Considerations and the Benefits of an IAQ Program," A Guide to Managing Indoor Air Quality in Healthcare Organizations, pp. 93–105.

Franz, D. R. et al., "Clinical Recognition and Management of Patients Exposed to Biological Warfare Agents," JAMA, vol. 278, pp. 399–411, Aug. 6, 1997.

Christopher, G. W. et al, "Biological Warfare: A Historical Perspective," JAMA, vol. 278, pp. 412–417, Aug. 6, 1997.

Zlinskas, R.A., PHD, "Iraq's Biological Weapons: The Past as Future?", JAMA, vol. 278, pp. 418–424, Aug. 6, 1997.

Holloway, H.C. MD et al., "The Threat of Biological Weapons: Prophylaxis and Mitigation of Psychological and Social Consequences," JAMA, vol. 278, pp. 425–427, Aug. 6, 1997.

Simon J. D., PHD, "Biological Terrorism: Preparing to Meet the Threat," JAMA, vol. 278, pp. 428–430, Aug. 6, 1997.

Krafthefer, B. et al., "Radon Entry into Large Buildings and Energy Conservation," Indoor Air 1996, pp. 1–7, Jun. 1996.

Krafthefer, B., et al., "Implications of Room Air Motion on Control of Thermal Comfort in Rooms with Natural Convection Heat Sources," pp. 119–127.

USAMRIIS's Medical Management of Biological Casualties Handbook, U.S. Army Medical Research Institute of Infectious Diseases, Ft. Detrick, Frederick, MD., 4th ed., Feb. 2001.

Lerner, B., Birmingham, J., Tonkyn, R., Barlow, S. and Orlando, T., "Decomposition of Trichloroethylene by a High Flow Packed–Bed Gas Phase Corona Reactor," pp. 697–703.

Ensor D. S. Ph.D, et al., "Changing Requirements for Air Filtration Test Standards," ASHRAE Journal, Jun., 1994.

"NBC Decontamination", FM 3–5/MCWP 3–37.3 Headquarters, Department of the Army Commandant, US Marine Corps, Jul. 28, 2000.

Federal Response Plan, 9230:1–PL, Federal Emergency Management Agency, Washington, DC., Apr. 1999.

Schultz, K. J. et al., "$CO_2$–Based Ventilation Control: Choice of $CO_2$ Setpoint", ASHRAE Symposium, Jun., 1992.

Krafthefer, B.C. and MacPhaul, D., "Ultrafine Particle Emission from Baseboard and Other Resistance–Type Heaters", Proceedings, the 5th International Conference on Indoor Air Quality and Climate: Indoor Air '90, Toronto, Canada, Jul. 29–Aug. 3, 1990.

"Potential Military Chemical/Biological Agents and Compounds," FM 3–9, NAFAC P–467, AFR 355–7, Headquarters, Department of the United States Army, Navy, and Air Force, Washington D.C. Dec. 12, 1990.

Krafthefer, B.C., "Effect of Filtration on Particle Size Distribution", ASHRAE Transactions, pp. 1866–1865.

Krafthefer, B.C., and Schultz, K., "Environmental Chamber for the Study of Room Air Distribution", Proceedings of "Building Systems: Room Air and Air Contaminant Distribution" symposium sponsored by NSF, U of I at Urbana–Champaign, Dec. 5–8, 1988.

Krafthefer, B.C., et al., "Air–Conditioning and Heat Pump Operating Cost Savings by Maintaining Coil Cleanliness", ASHRAE Transactions, vol. 93, 1, 1987.

Woods, J.E. and Krafthefer, B.C., "Filtration as a Method for Air Quality Control in Occupied Spaces," Fluid Filtration: Gas, vol. I, ASTM STP 975, R.R. Raber, ed., American Society for Testing and Materials, Philadelphia, 1986.

Krafthefer, B. C. and Boone, U., "Energy Use Implications of Methods to Maintain Heat Exchanger Coil Cleanliness", ASHRAE Transactions, vol. 92, 1, 1986.

Woods, J.E., Janssen, J.E., and Krafthefer, B.C., "Rationalization of Equivalence Between the 'Ventilation Rate' and 'Air Quality' Procedures in ASHRAE Standard 62.", Proceedings IAQ '86, Atlanta, GA, Apr. 21–23, 1986.

Woods, J.E., Krafthefer, B.C., Janssen, J.E., "Solutions to Indoor Air Quality Problems in Tight Housing", Presented at Energy Technology XII, Mar. 25–27, 1985.

Benjamin Y.H. Liu, et al., "Particle Distributions from Smoldering and Flaming Fire Situations", Aerosols Science, Technology, and Industrial Applications of Airborne Particles, Elsevier, New York, pp. 731–733, 1984.

Krafthefer, B.C., "Electronic Air Cleaners and the Indoor Environment", Proceedings of an Engineering Foundation Conference on Management of Atmospheres in Tightly Enclosed Spaces, Santa Barbara, CA, Oct. 17–21, 1983.

Wehrle, P. F., J. Posch, K. H. Ricter, and D. A. Henderson, "An Airborne Outbreak of Smallpox in a German Hospital and its Significance with Respect to Other Recent Outbreaks in Europe," Bull. Org. mond. Sante Bull. Wld. Hlth. Org., 1970, 43, pp. 669–679.

Walter, Katie, "Reducing the Threat of Biological Weapons," Science and Technology Review, Jun. 1998, pp. 4–9.

Byler, et al., "Autonomous Hazardous Waste Drum Inspection Vehicle," IEEE Robotics & Automation Magazine vol. 2, No. 1, pp. 6–17, Mar. 1, 1995.

* cited by examiner

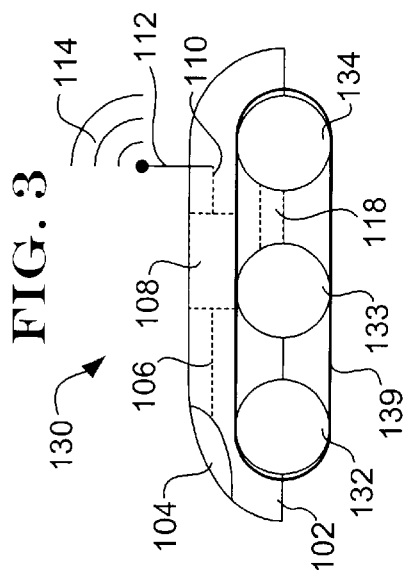
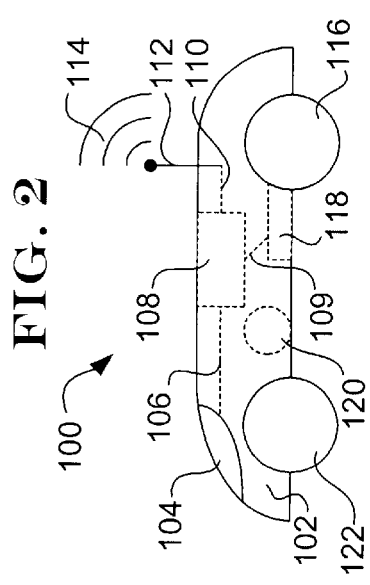
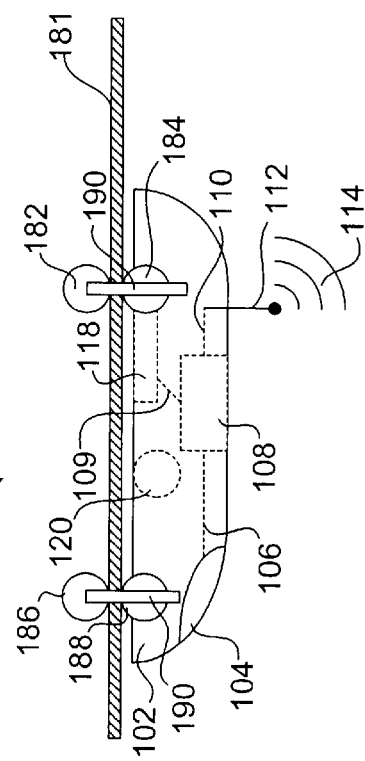
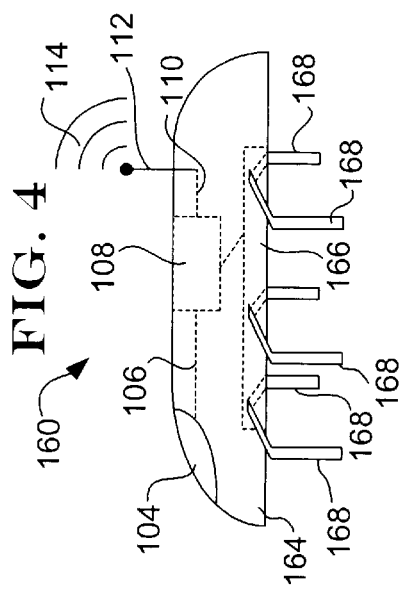

CHEMICAL OR BIOLOGICAL ATTACK DETECTION AND MITIGATION SYSTEM

FIELD OF THE INVENTION

The present invention generally relates to chemical or biological attack detection and mitigation systems, and more particularly to chemical or biological attack detection and mitigation systems for buildings.

BACKGROUND OF THE INVENTION

The recent demise of the cold war and decline in superpower tensions has been accompanied by an increase in concern over the viability of weapons of mass destruction, such as chemical and biological (CB) weapons. CB weapons include chemical agents, such as blood, blister, and nerve agents, and biological agents, such as anthrax or small pox. CB weapons may be delivered to occupants within a building by releasing the agents external to the building, but close to an air intake of the building. The air intake may be located near the ground, near the roof, or somewhere in between, depending on the building architecture. Agents may also be released within a public area of a building, and be dispersed to other, private areas of the same building. Agents released in one area of a building may be further dispersed by the heating, ventilating, and air conditioning (HVAC) system of the building. Therefore, the HVAC system may effectively deliver an agent from one room to the entire building. While the agent is being delivered through the building, the location of the agent source may remain unknown, as well as the extent of the harm caused.

There are various agent delivery mechanisms. For example, agents may be delivered in vehicles giving some warnings as to the delivery, such as missiles. Agents may also be delivered in vehicles giving no warning, such as a pedestrian held putative asthma inhaler activated near an air intake in the building.

Certain buildings, such as key military sites, can be equipped or designed well in advance to deal with the use of CB weapons. Such buildings may include elaborate, built-in fixed chemical and biological sensors. Such fixed sensors, even when thorough, are generally limited to sensing one area of a building, and may be too expensive to place in all desired areas of a building. Some buildings, however, such as hotels, may be more susceptible to a CB weapons attack, lacking even fixed sensors. What would be desirable, therefore, are chemical and biological sensors that can be deployed at multiple locations in a building. What would also be advantageous are sensors that are able to search for and identify the location of harmful agents. Devices able to assist building inhabitants during an attack would also be valuable.

SUMMARY OF THE INVENTION

The present invention includes systems for detecting agents harmful to human life in buildings. The systems can include a self-propelled harmful agent detector for traversing spaces anywhere in buildings. The self-propelled agent detectors can include a harmful agent sensor for sensing chemical and/or biological agents injurious to human health, with the harmful agent sensor having a data output. A transmitter can be coupled to the harmful agent sensor data output for transmitting data from the self-propelled harmful agent detector to a receiver. A power source can supply a motor having a moving output, with a traction device coupled to the motor moving output for moving the self-propelled harmful agent detector. One embodiment has a rotating shaft as the motor moving output, with the rotating shaft coupled to at least one wheel. Some embodiments use wheels as a traction device, other embodiments utilize tracks, and still other embodiments utilize capstans for moving the detector along suspended wires or strings. Some devices use take-up pulleys or winches to move the device up and down along strings or wires.

Some detectors have sensors that can measure levels of harmful agent concentration, wherein the sensor data contains data indicating harmful agent levels, and the transmitter can transmit the agent level data. Sample traps, such as vacuum vessels or adhesives, may be included in some devices to capture samples for later analysis. Some detectors can identify the type of the harmful agent and transmit that as well. Many detectors according to the present invention also broadcast the identity and absolute or relative location of the detector. Devices may have cameras and transmitters coupled to the cameras for transmitting images near the detectors to a receiver. Such mobile transmitting cameras may be used to transmit images including victim location.

Systems incorporating moving detectors according to the present invention are also provided. Systems can include receivers for receiving data transmitted by the moving detectors. The received information can include the mobile detector ID, the type of agent detected, the agent level detected, and the location of the detector. Some systems include machine intelligence for propelling the detector toward areas having higher harmful agent concentrations. Some mobile detectors have repeating capabilities, for receiving and re-transmitting signals received from other mobile detectors in order to extend the range of transmitters, which may be disposed in areas not conducive to RF transmissions, such as within air ducts. Some systems have mobile agent detector location systems, such as a triangulation system within a building, in order to locate the position of a transmission without requiring a mobile detector to have knowledge of its position.

Some embodiments of the invention, in addition to collecting and transmitting data, can assist building inhabitants. One class of devices according to the present invention can carry information, guidance, life support equipment, and even decontamination equipment to people located within a building. One such device is large enough to carry air bottles, air packs, face masks, breathing filters, protective garments, and communication gear within the device. Some devices transmit photographic views of the area surrounding the device to a central site. Other embodiments include speakers and/or changeable message signs which can be used to transmit instructions to building inhabitants. One use of such devices is to find a safe egress route from a building that is contaminated, and instruct building inhabitants as to the route and/or instruct the building inhabitants to "follow me."

Methods according to the present invention include providing the mobile detectors and/or receiving systems described above. The mobile harmful agent detectors can be disposed within the building and allowed to move throughout the building, and transmit information related to any harmful agent present. Some methods include mobile detectors disposed and programmed to roam outside of a building. Mobile detectors can be disposed along building floors, within air ducts, disposed along suspended wires, strings, or shafts, and hung from hanging wires, strings, ribbons, or pendulums, both within open atriums and within vertical air shafts. Some systems move the self-propelled detectors by providing the motor on one end of a string or wire and the detector on the other end. The detector is then moved by advancing the motor to move the string or wire. Other systems provide a fixed string or wire, with the detector and motor moved together. Flying mobile detectors, for example, sensors mounted on micro air vehicles (MAVs), are also included within the invention.

Some methods include providing self-propelled detector sensors to measure levels of harmful agent concentration, wherein the transmitted sensor data contains data indicating harmful agent levels, which is received and stored. Other methods include directing self-propelled mobile detectors to areas of interest, where the direction is provided from a central controller, either machine or human. In some systems, a central computer creates maps of agent type and/or intensity using the data provided by the mobile detectors.

BRIEF DESCRIPTION OF THE DRAWINGS

FIG. 2 is a highly diagrammatic, side view of a mobile harmful agent detector device having a power source, controller, transmitter, motor, and wheels for traction;

FIG. 3 is a highly diagrammatic, side view of a mobile harmful agent detector device similar to that of FIG. 2, but having a track for traction;

FIG. 4 is a highly diagrammatic, side view of a mobile harmful agent detector device similar to that of FIG. 2, but having legs for traction;

FIG. 5 is a highly diagrammatic, side view of a mobile harmful agent detector device similar to that of FIG. 2, but having driven pulleys or capstans for traction along a wire or cable which may be substantially horizontal;

DETAILED DESCRIPTION OF THE INVENTION

Figure 1:
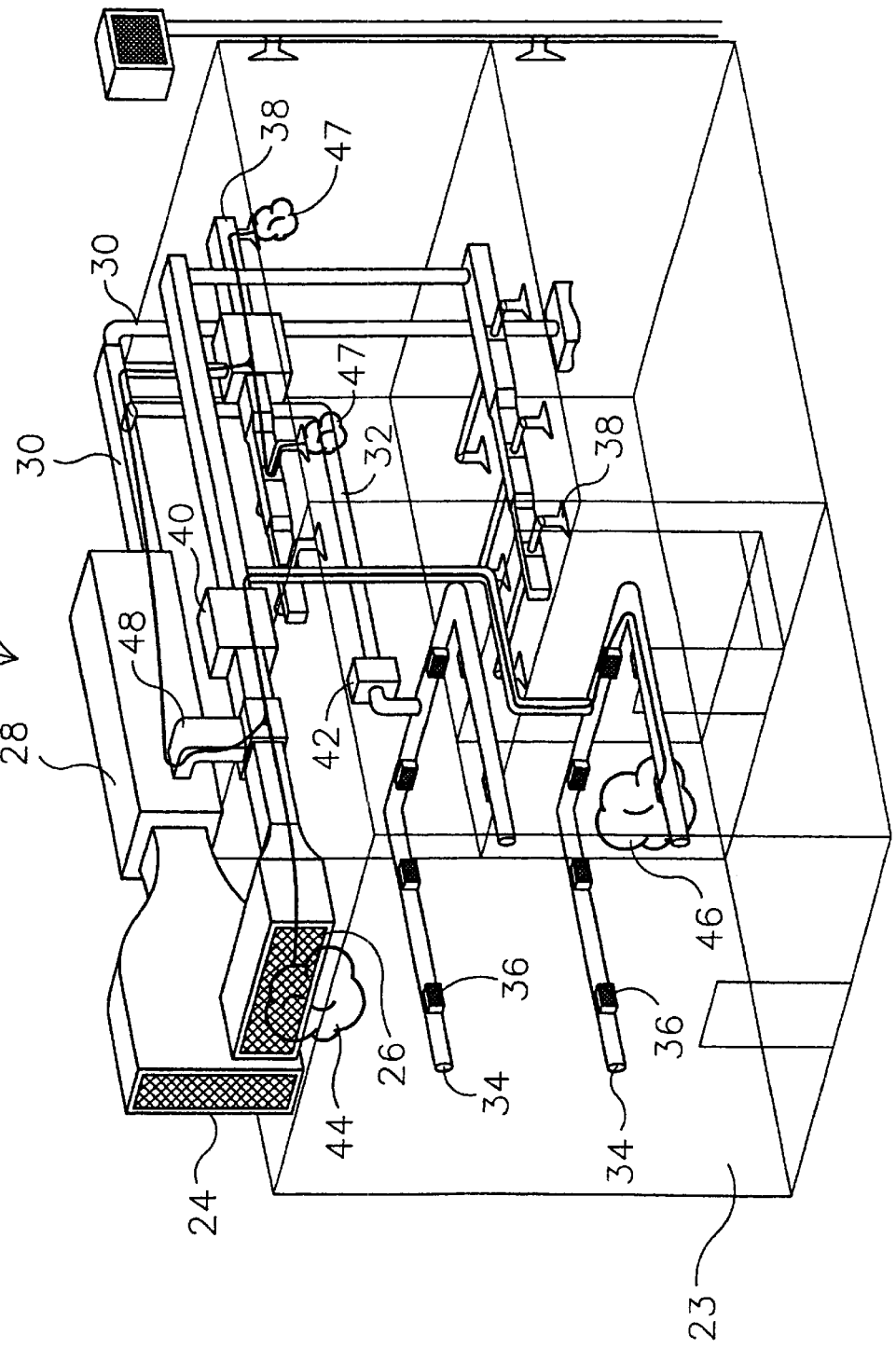
FIG. 1 is a highly diagrammatic, perspective, cutaway view of a conventional building HVAC system shown delivering a harmful agent from a public area return air duct to private areas in the building interior.

Various embodiments of the invention are described below in some illustrative examples of the invention. Such examples are intended to be illustrative rather than limiting. Identical reference numerals are used across the multiple figures to describe identical or similar elements, which are not reintroduced with each figure.

FIG. 1 illustrates a building 20 including a public atrium area 23 and having a conventional building heating, ventilating, and air conditioning (HVAC) system 22 not having any duct isolation equipment in place. HVAC system 22 is illustrated transporting harmful agent 46 through return air ducts 34 and dispersing it as externally released cloud 44. Air intake 24 and exhaust 26 are connected to a series of ducts including large, usually rectangular chambers or ducts such as chamber 28, and intermediate sized, usually rectangular, ducts 30. Intermediate ducts 30 split off into a series of smaller, often circular, ducts 32, which feed a series of room diffusers 38. Return air vents 36 and return air ducts 34 return air to either be expelled outside the building or be mixed with fresh air intake. Heating, cooling, humidification, and dehumidification functions are often performed in large chambers such as chamber 28, and in more local intermediate sized chambers 42. Mixing and/or recirculation can be performed by a return air duct 48.

FIG. 1 illustrates an internally released harmful agent cloud 46 dispersed in public atrium 23 near return air vents 36. HVAC system 22 is illustrated transporting harmful agent 46 through return air ducts 34 and dispersing it as externally released cloud 44. Return air ducts 34 are also connected through return air duct 48, into intake chamber 28, and may internally release harmful agent cloud 47 through diffusers 38. As illustrated, the harmful agent is delivered from a public portion of the building to the private areas of the building by the HVAC system and to the exterior near the building as well.

FIG. 2 illustrates a mobile, self-propelled harmful agent detector device 100, having a chassis or body 102, a first wheel set 116, a second wheel set 122, a harmful agent sensor 104, a controller 108, a power source 120, a motor 118, and a transmitter 112. Controller 108 is coupled to agent detector 104 through a data communication line or channel 106, which can be, for example, any suitable electrical or optical line, wire, or channel. As used herein, "harmful agent sensor or detector" means a sensor or detector for sensing, measuring, or detecting agents harmful to humans, including chemical and biological agents. The terms "harmful agent sensor or detector" and "agent sensor or detector" are intended to convey the same meaning as used herein. Although any suitable detector either known or unknown at the present time may be used, the agent detectors can include, for example, spectrographic analyzers including visible, infrared, near infrared, ultraviolet, and/or fluoroscopic. So-called "chemical noses" or "electrical noses" may be used to identify agents. Portable mass spectrometers may also be used. Portable bioassay devices, reagents, and readable test strips may also be used as agent detectors, if desired.

In some embodiments, a harmful agent trap is included. Agent traps can include vacuum bottles having controllable inlet valves, or other sampling devices, well known in industrial hygiene monitoring applications. Filter traps and adhesive traps may also be included, and can be used to trap samples for later analysis. In some embodiments, a camera is included with, or in place of, harmful agent sensor 104, with a picture being transmitted either in addition to, or in place of, harmful agent concentration data. In embodiments having only a camera, for example, reference numeral 104 may be understood to refer to a camera.

Controller 108 may be coupled to transmitter 112 through a data line 110, and is illustrated transmitting data indicated at 114. Any suitable transmitter may be used, including radio frequency (RF) and optical transmitters. While the term "transmitter" is used to denote one function of the mobile detector, the transmitter in a preferred embodiment is a transceiver, able to both transmit and receive information.

Power source 120 may be a battery and is preferably coupled to motor 118. Power sources may be either fixed to the mobile detector, or located apart from the mobile detector and coupled to the detector by wires. Controller 108 can be coupled to motor 118 through a control line 109, which can be used to control the motor driving the wheel or wheels. In one embodiment, first wheel set 116 are drive wheels and second wheel set 122 are turnable or steerable wheels, under the control of controller 108. In some embodiments, mobile detector 100 is self-aware of its position, and can transmit that position to a receiver. In other embodiments, mobile detector 100 transmits a signal which can be triangulated upon by multiple receivers. In still other embodiments, mobile detector 100 can count its relative progress along a known route, by inches, clicks, or wheel rotations, with the relative progress into the route ascertainable by the mobile detector and/or a central receiving unit. In a preferred embodiment, the ID of the mobile detector is transmitted along with any other data. In one embodiment, the mobile detector includes a transceiver and may be programmed to retransmit data received from other mobile detectors, having different IDs, thereby allowing the mobile detectors to act as relays. This may be useful for embodiments having short transmission ranges, or detectors disposed within metal air ducts.

Mobile detector 100 utilizes wheels 116 and 122 as traction devices. The wheels may be formed of a rubber material or other polymer suitable for providing traction. Mobile detector 100 may be used to traverse floors, air ducts, crawl spaces, false ceilings, or any surface the wheels are able to engage. In mobile device 100, motor 118 is mounted on body 102 such that motor 118 travels together with body 102. In some devices, discussed below, the propelling motor is fixed to another object and remains in one location while propelling the body, for example, through a tether. In either case, the mobile detector may be self-propelled.

FIG. 3 illustrates a mobile detector 130, similar to mobile detector 100 of FIG. 2, but utilizing tracks or treads 139 disposed over three wheel pair sets 132, 133, and 134. Tracks or treads may be more useful in traversing unfriendly terrain than wheels alone. In some devices, tracks are sufficiently long to enable climbing stairs.

FIG. 4 illustrates a mobile detector 160, similar to mobile detector 100 of FIG. 2, but utilizing legs 168 disposed in three pairs on a chassis or body 164. Legs may be motor driven by a motor 166 to enable the device to crawl over uncertain terrain, and may be more useful in traversing unfriendly terrain than wheels.

FIG. 5 illustrates a mobile detector 180, similar to mobile detector 100 of FIG. 2, but utilizing pulleys or capstans 182, 184, 186, and 188, which are supported by legs 190 secured to body 102 and disposed about a wire, cable, string, shaft, or ribbon 181. Wire 181 may be substantially horizontal in some embodiments, and may be strung through air ducts, under computer room raised floors, through crawl spaces, between buildings, and across building atriums. In some embodiments, the gap between the upper and lower wheels, 182 and 184, and 186 and 188, respectively, may be relatively large, and gravity relied upon to provide traction between driven upper wheels 182 and 186 and wire 181. In other embodiments, the gap between the upper and lower wheels, 182 and 184, and 186 and 188, respectively, may be relatively small, and a tight fit between wheels and wire is relied upon to provide traction. In embodiments having a tight fit, enabling the wheels to grasp wire 181, either upper wheels 182 and/or 186, or lower wheels 184 and/or 188, or both, may be driven by motor 118. In some embodiments, mobile detector 180 travels between two extreme limits of travel, reversing direction when either limit is reached. In some devices, a count of wheel revolutions or similar measure is used to measure travel and can be used to calculate relative location along the route.

Figure 6:
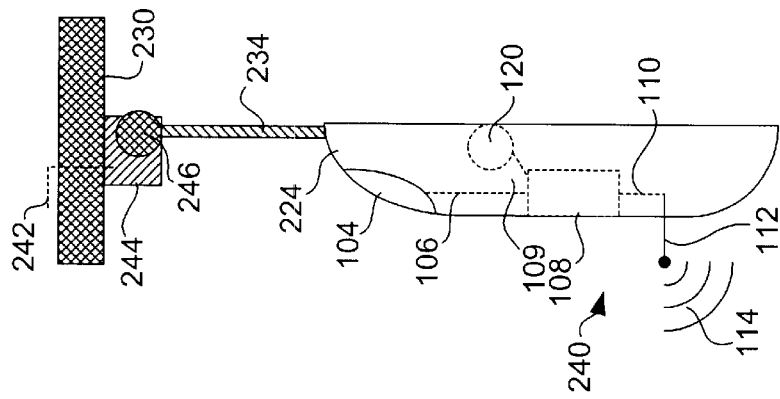
FIG. 6 is a highly diagrammatic, side view of a mobile harmful agent detector device similar to that of FIG. 5, but having driven pulleys or capstans for traction along a wire or cable which may be substantially vertical.

FIG. 6 illustrates a mobile detector 200, similar to mobile detector 180 of FIG. 5, but utilizing pulleys or disposed about a wire, cable, string, shaft, or ribbon 232. Wire 232 is illustrated as fixed to support member 230, which may be a ceiling in some applications. Wire 232 may be substantially vertically disposed in some embodiments, and may be strung through air ducts, wall spaces, elevator shafts, and building atriums. In a preferred embodiment, the gap between wheel pairs, 182 and 184, and 186 and 188, may be relatively small, and a tight fit between the wheels and wire 232 is relied upon to provide traction. In embodiments having a tight fit, enabling the wheels to grasp wire 232, either wheels 182, 186, 184 and/or 188, may be driven by motor 118. In some embodiments, wire 232 is serrated, having teeth or other demarcations, providing improved traction. In some embodiments, at least some of the driven wheels are also serrated or have teeth to provide better traction. In some devices, both wire or ribbon 232 and the driven wheels have matching sized teeth, to provide a track for the wheel teeth to engage for better traction. In some embodiments, mobile detector 200 travels between two extreme limits of travel, reversing direction when either limit is reached. In some devices, a count of wheel revolutions or similar measure is used to measure travel and can be used to calculate relative location along the route.

Figure 7:
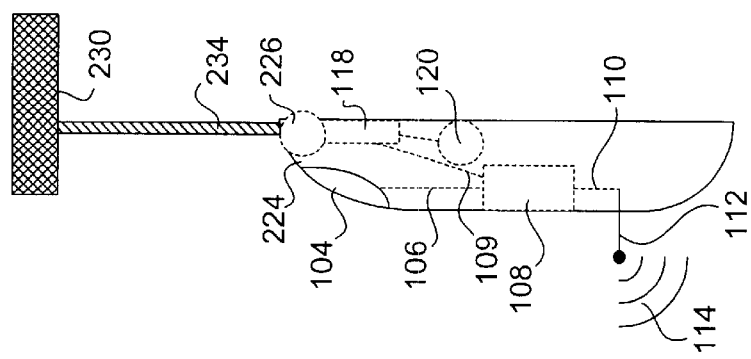
FIG. 7 is a highly diagrammatic, side view of a mobile harmful agent detector device similar to that of FIG. 6, but having motor driven traction pulleys or spools mounted on the mobile detector for taking up a wire or cable which may be substantially vertical.

FIG. 7 illustrates a mobile detector 220, similar to mobile detector 200 of FIG. 6, but utilizing a take-up pulley or spool 226 to take up a wire, cable, string, or ribbon 234 suspended from support member 230, which may be a ceiling in some applications. Wire 234 may be substantially vertically disposed in some embodiments, and may be strung as discussed with respect to wire 232 or FIG. 6. Motor driven take-up spool or pulley 226 is secured to body 224, and can wind wire 234 about the spool as the spool is driven, thereby providing the traction, and pulling mobile detector 220 upward. Downward movement may be provided by reversing the motor direction or by allowing take-up spool 226 to unwind, either controllably or rapidly, depending on the embodiment. In some devices, a count of spool revolutions or similar measure is used to measure travel and can be used to calculate relative location along the route.

Figure 8:
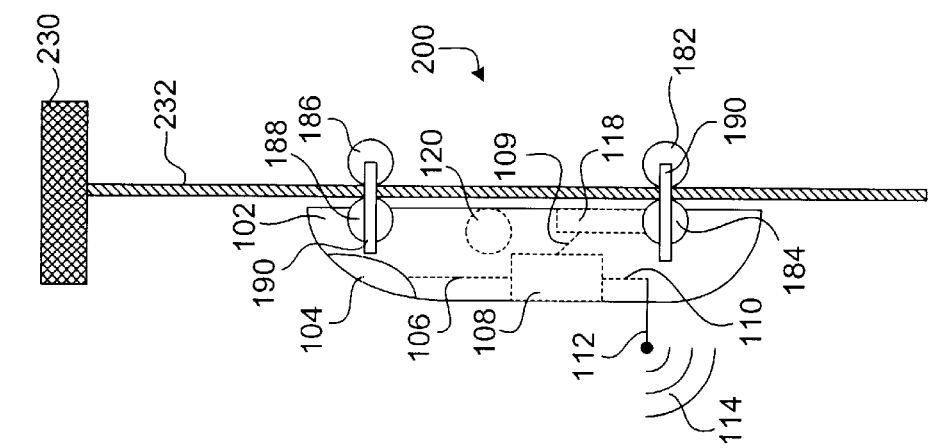
FIG. 8 is a highly diagrammatic, side view of a mobile harmful agent detector device similar to that of FIG. 7, but having motor driven traction take up pulleys or spools mounted on the opposing end of a wire or cable which may be substantially vertical.

FIG. 8 illustrates a mobile detector 240, similar to mobile detector 220 of FIG. 7, but utilizing motor 244 driving a take-up pulley or spool 246 to take up wire, cable, string, or ribbon 234 suspended from support member 230, which may be a ceiling in some applications. A control and/or power line 242 may be coupled to motor 244 to provide power and/or control for the device. Motor driven take-up spool or pulley 246 is secured to motor 244, and can wind wire 234 about the spool as the spool is driven in some embodiments, thereby providing the traction, and pulling mobile detector 240 upward. Downward movement may be provided by reversing the motor direction or by allowing take-up spool 246 to unwind, either controllably or rapidly, depending on the embodiment. Mobile detector 240 may be said to be self-propelled, but having the motor fixed at the opposing end of a tether, rather than moving with the mobile detector. As previously discussed, the location of the detector may be measured and transmitted along with other data related to agent detection.

Figure 9:
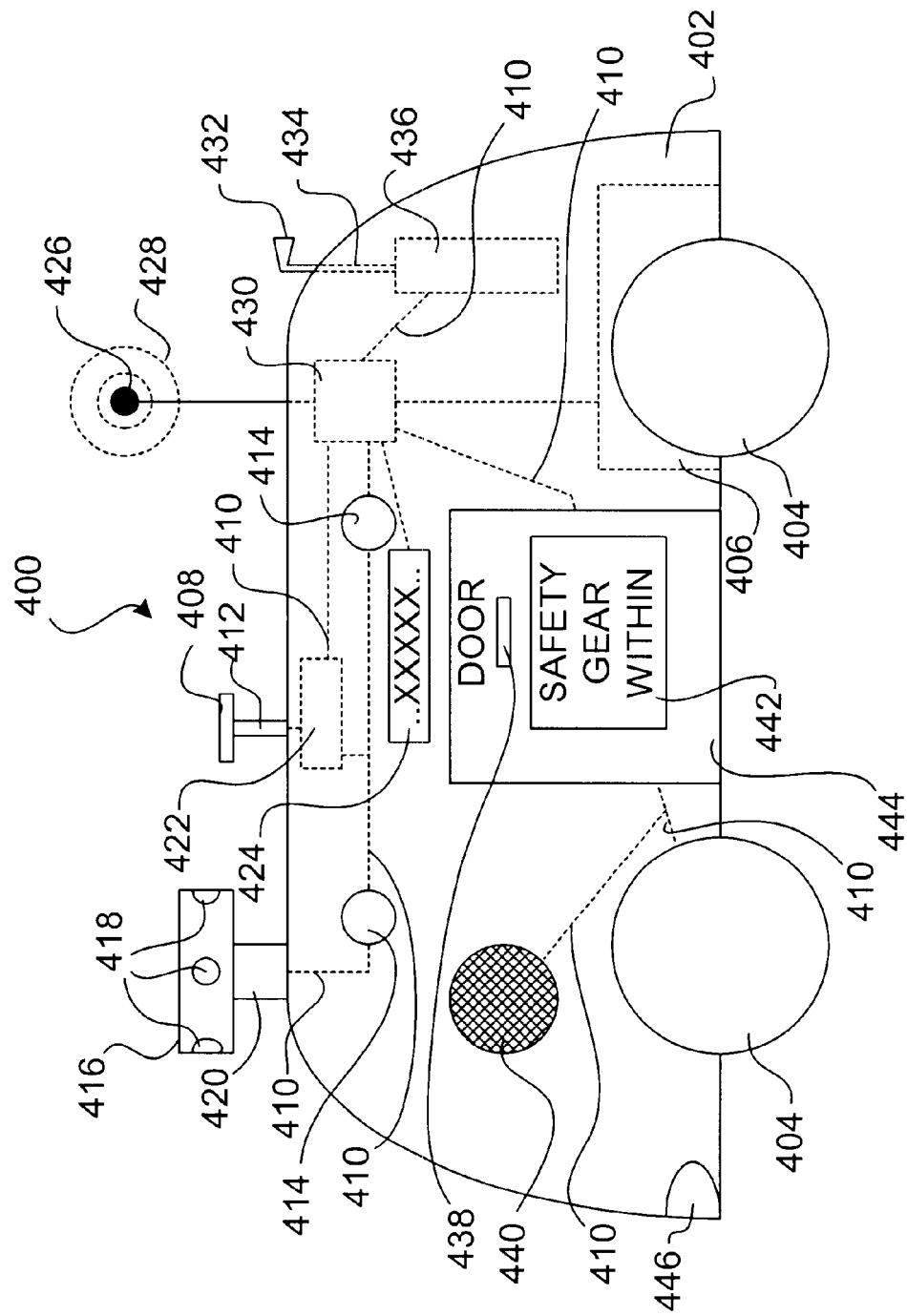
FIG. 9 is a highly diagrammatic, side view of a mobile harmful agent detector which can be used to transmit pictures to a remote site, transmit information to building inhabitants, and carry safety equipment to inhabits.

FIG. 9 illustrates a mobile self-propelled harmful agent detector 400, having lights 446 and wheels 404 mounted on body 402, the wheels driven by motor 406. Mobile detector 400 includes a controller 430 coupled to other components through control lines 410. Unless otherwise indicated, lines 410 illustrated in FIG. 9 are power and/or control lines, which can be used to provide power and/or transmit and receive data between the various components. Controller 430 can be coupled to a transmitter 426 for transmitting and receiving data 428 as illustrated. As previously discussed, the transmissions may be through any suitable medium including RF and IR. In one embodiment, mobile detector 400 is capable of carrying life support equipment for building inhabitants, and of providing assistance during an emergency.

A camera head 416 having multiple cameras 418 is disposed on a neck member 420, which can preferably be controllably turned to face directions determined by a remotely located operator. Images provided by cameras 418 may be transmitted back to a receiver. In one embodiment, neck 420 is fixed, with the multiple cameras being selectable to provide different views. In some embodiments, microphones 414 or other sensors are disposed along the body sides to listen for noises, for example, human voices. The sound signals thus received may also be transmitted back to a receiver.

A sensor head 408 is also illustrated, which may be rotated about a rotatable neck member 412. Sensor head 408 may include multiple harmful agent sensors including arrays or different sensors to be used in chemical analysis. Sensor head 408 may include air intake or suction ports to be used, for example, to feed chromatographic or other instruments within body 402. Sensor head 408 is illustrated as coupled to a sensing analysis unit 422 which is in turn coupled to controller 430. Sensor head 418 may be rotated in some devices, so as to take samples from different directions.

Mobile detector 400 may include communications devices intended to communicate with humans who may be located within a building, unsure of what to do. In particular, building inhabitants may be unsure if they should attempt to leave a building, or unsure of what route may be safe to take out of a building. To this end, mobile detector 400 may include a changeable message sign 424, having, for example, a large, light emitting diode (LED) scrolling display with useful information. Such a display may be controlled by a central controller through transceiver 426.

Similarly, a loudspeaker 440 may be used to inform building inhabitants as to a safe route to take out of the building, or may inform the inhabitants to remain in place. Loudspeaker 440 may be coupled through transceiver 426 and may be used in conjunction with microphones 414 to allow a remote operator engage in conversations with people.

Mobile detector 400 may also contain decontamination equipment, for example, a canister of decontamination fluid or foam 436 coupled to a decontamination nozzle 432 through a pipe or tube 434. In some embodiments, pipe 434 can be controllably rotated and aimed by a remote operator, with the decontamination fluid or foam controllably ejected by a remote operator, or even by a local person following proper instructions.

A door 444 may be attached to body 402, and be opened through use of a handle 438. A sign 442 may be used to indicate to persons located nearby that there is safety equipment inside. In one embodiment, door 444 is attached to body 402 with hinges. Safety gear disposed within body 402 can include oxygen tanks, regulators, air bottles, air packs, respirators, first aid equipment, filter masks, decontamination equipment, protective garments, and communication equipment, such as portable radios or telephones.

In one use of mobile agent detector 400, mobile agent detector, either alone or using externally provided information, locates a safe egress path through a building believed to be otherwise contaminated, or under harmful agent attack. With the route located, mobile agent detector 400 may travel through the building, informing personnel within of the safe egress route. One method includes having mobile agent detector 400 informing people that a safe route is to be had by following the mobile detector to a destination, which may be an outside exit or an inside safe room.

Figure 10:
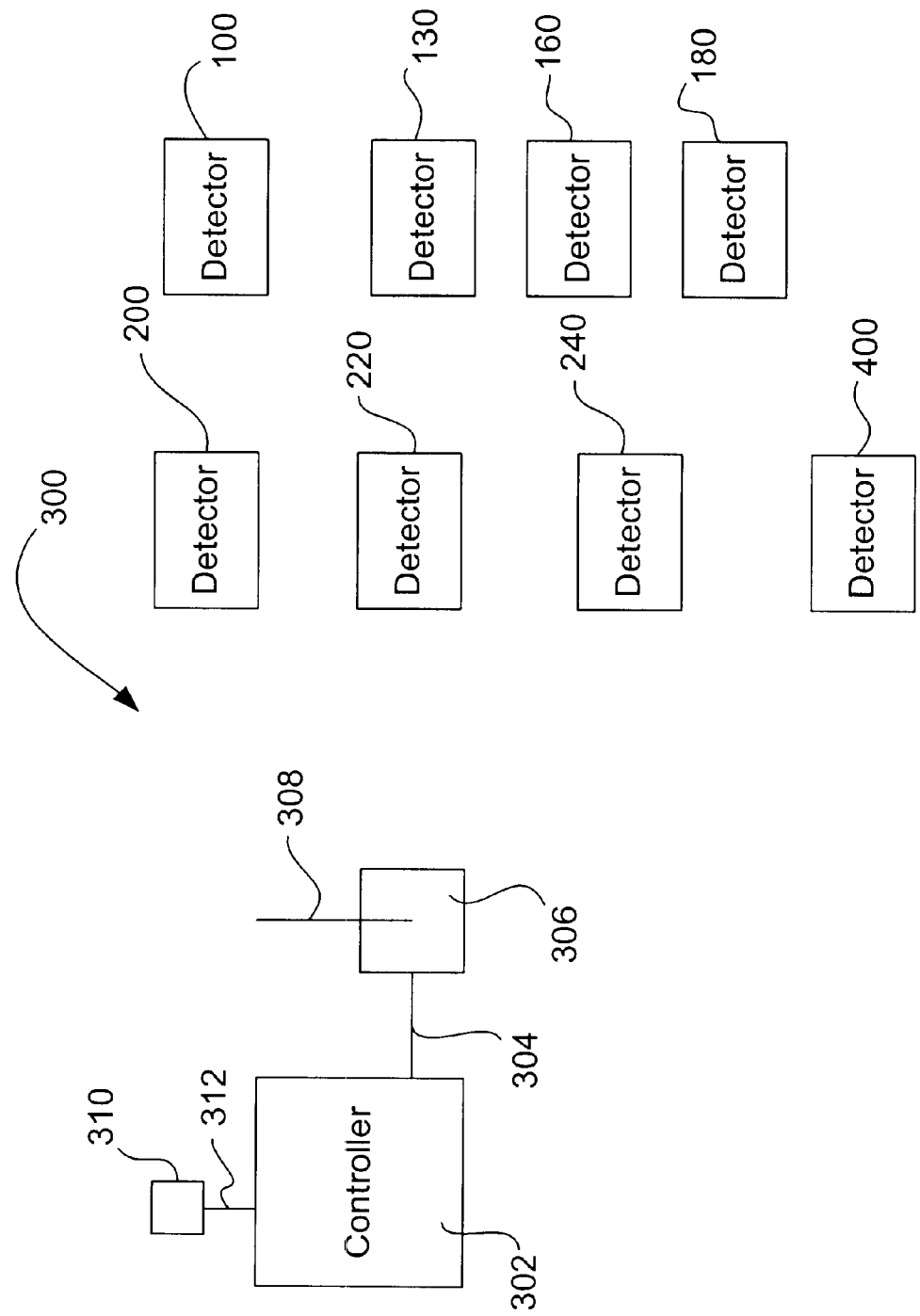
FIG. 10 is a block diagram of a system for communication with and coordination of mobile harmful agent detectors.

FIG. 10 illustrates a mobile agent detector system 300, including a central controller or computer 302, and a transceiver 306 with antenna 308. An operator interface device 310, for example a CRT or console, is coupled to controller 302 by a communications line or channel 312. Transceiver 306 is coupled to controller 302 by a data communications line or channel 304.

Controller 302 preferably includes a computer, and operator interface device 310 preferably includes a display screen. Controller 302 can be used to coordinate the movement of numerous mobile detectors, for example, mobile detectors 100, 130, 160, 180, 200, 220, 240, and 400. In one embodiment, controller 302 directs the mobile detectors to execute preassigned roaming modes, while tracking, recording, and plotting any possible harmful agents detected. When there is a precipitating event, such as a high concentration measured for a harmful agent, controller 302 may take a more active role.

In one method, controller 302 may assign the more intrusive mobile detectors, for example the wheeled, steerable detectors, to roam the building floors, out in the open, searching for high concentrations of harmful agents. In one method, mobile detectors able to steer themselves toward higher concentrations are allowed to do so. As the detectors gather data, hot spots, or high concentration areas of harmful agents, are searched for, recorded, plotted, and analyzed by controller 302 and, in some embodiments, analyzed by a human operator.

In one illustrative example, a mobile detector, such as detector 240, may detect a harmful agent concentration near a specified floor level of a large, central return vertical air duct, while an elevator shaft mounted detector confirms the specified floor as a high concentration area. One mobile detector, such as detector 180, may indicate the presence of an agent in a smaller horizontal return air duct near that floor, at a specific location of travel. At the same time, a mobile detector within a supply duct for that floor may indicate that no agent has been detected. This may rapidly pinpoint the source of the agent.

In response, the proper air handling motors, dampers, and blowers may be controlled, and turned on or off, in order to limit the spread of the harmful agent, or even force the harmful agent from the building. Mobile detectors such as wheeled detectors 100, 130, or 160 may be instructed to roam the specified and adjoining floors, while remote detector 400 may be sent to the specified floor to provide assistance. By way of comparison, the same number of fixed detectors in the same building may only indicate that there is a harmful agent somewhere in the building, later confirmed by reports of people being harmed, after the agent has been allowed to further spread.

Numerous advantages of the invention covered by this document have been set forth in the foregoing description.

It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A self-propelled harmful agent detector for traversing spaces in buildings comprising:

a harmful agent sensor for sensing chemical and/or biological agents injurious to human health, the harmful agent sensor having a data output;

a transceiver coupled to the harmful agent sensor data output for transmitting data from the self-propelled harmful agent detector and receiving instructions from a central control station;

a power source;

a motor having a moving output and being supplied with power from the power source; and a traction device coupled to the motor moving output for moving the self-propelled harmful agent detector; and a controller for controlling the motor such that the self-propelled harmful agent detector is moved along one or more predefined paths, the controller being coupled to the transceiver to receive instructions related to controlling the motor and the traction device, wherein the controller is adapted to modify a predefined path in response to instructions received by the transceiver.

2. A self-propelled harmful agent detector as in claim 1, wherein the power source is completely contained within the self-propelled detector.

3. A self-propelled harmful agent detector as in claim 1, wherein the power source is a power supply line leading into the self-propelled detector.

4. A self-propelled harmful agent detector as in claim 1, wherein the motor is affixed to the self-propelled detector.

5. A self-propelled harmful agent detector as in claim 1, further comprising a camera having an output coupled to the transmitter for transmitting pictures taken by the camera.

6. A self-propelled harmful agent detector as in claim 1, wherein the self-propelled detector is self-powered.

7. A self-propelled harmful agent detector as in claim 1, wherein the traction device includes wheels and the harmful agent detector is self-propelled through the wheels.

8. A self-propelled harmful agent detector as in claim 1, wherein the sensor can measure levels of harmful agent concentration, wherein the sensor data contains data indicating the harmful agent levels, and wherein the transmitter can transmit the agent level data.

9. A self-propelled harmful agent detector for traversing spaces in buildings comprising:

a harmful agent sensor for sensing chemical and/or biological agents injurious to human health, the harmful agent sensor having a data output;

a transmitter coupled to the harmful agent sensor data output for transmitting data from the self-propelled harmful agent detector;

a power source;

a motor having a moving output and being supplied with power from the power source; and a traction device coupled to the motor moving output for moving the self-propelled harmful agent detector; and a controller for controlling the motor such that the self-propelled harmful agent detector is moved along one or more predefined paths;

wherein the motor is immobile and the self-propelled detector is secured to the motor by an elongate member.

10. A self-propelled harmful agent detector for traversing spaces in buildings comprising:

a harmful agent sensor for sensing chemical and/or biological agents injurious to human health, the harmful agent sensor having a data output;

a transmitter coupled to the harmful agent sensor data output for transmitting data from the self-propelled harmful agent detector;

a power source;

a motor having a moving output and being supplied with power from the power source; and a traction device coupled to the motor moving output for moving the self-propelled harmful agent detector; and a controller for controlling the motor such that the self-propelled harmful agent detector is moved along one or more predefined paths;

wherein the traction device includes tracks.

11. A self-propelled harmful agent detector for traversing spaces in buildings comprising:

a harmful agent sensor for sensing chemical and/or biological agents injurious to human health, the harmful agent sensor having a data output;

a transmitter coupled to the harmful agent sensor data output for transmitting data from the self-propelled harmful agent detector;

a power source;

a motor having a moving output and being supplied with power from the power source; and a traction device coupled to the motor moving output for moving the self-propelled harmful agent detector; and a controller for controlling the motor such that the self-propelled harmful agent detector is moved along one or more predefined paths;

wherein the traction device includes at least one capstan for gripping a string or wire.

12. A self-propelled harmful agent detector for traversing spaces in buildings comprising:

a harmful agent sensor for sensing chemical and/or biological agents injurious to human health, the harmful agent sensor having a data output;

a transmitter coupled to the harmful agent sensor data output for transmitting data from the self-propelled harmful agent detector;

a power source;

a motor having a moving output and being supplied with power from the power source; and a traction device coupled to the motor moving output for moving the self-propelled harmful agent detector; and a controller for controlling the motor such that the self-propelled harmful agent detector is moved along one or more predefined paths;

wherein the traction device includes a motor driven take-up spool affixed directly to the self-propelled detector.

13. A self-propelled harmful agent detector for traversing spaces in buildings comprising:

a harmful agent sensor for sensing chemical and/or biological agents injurious to human health, the harmful agent sensor having a data output;

a transmitter coupled to the harmful agent sensor data output for transmitting data from the self-propelled harmful agent detector;

a power source;

a motor having a moving output and being supplied with power from the power source; and a traction device coupled to the motor moving output for moving the self-propelled harmful agent detector; and a controller for controlling the motor such that the self-propelled harmful agent detector is moved along one or more predefined paths;

wherein the traction device includes a motor driven take-up spool secured to the self-propelled detector with an elongate tether.

14. A self-propelled harmful agent detector for traversing spaces in buildings comprising:

a harmful agent sensor for sensing chemical and/or biological agents injurious to human health, the harmful agent sensor having a data output;

a transmitter coupled to the harmful agent sensor data output for transmitting data from the self-propelled harmful agent detector;

a power source;

a motor having a moving output and being supplied with power from the power source; and a traction device coupled to the motor moving output for moving the self-propelled harmful agent detector; and a controller for controlling the motor such that the self-propelled harmful agent detector is moved along one or more predefined paths;

wherein the transmitter is adapted to transmit an identification code identifying the identity of the device.

15. A self-propelled harmful agent detector for traversing spaces in buildings comprising:

a harmful agent sensor for sensing chemical and/or biological agents injurious to human health, the harmful agent sensor having a data output;

a transmitter coupled to the harmful agent sensor data output for transmitting data from the self-propelled harmful agent detector;

a power source;

a motor having a moving output and being supplied with power from the power source; and a traction device coupled to the motor moving output for moving the self-propelled harmful agent detector; and a controller for controlling the motor such that the self-propelled harmful agent detector is moved along one or more predefined paths;

wherein the controller has knowledge of its position along the one or more predefined paths, and wherein the transmitter transmit the position.

16. A self-propelled harmful agent detector for traversing spaces in buildings comprising:

a harmful agent sensor for sensing chemical and/or biological agents injurious to human health;

a motor having a moving output;

a traction device coupled to the motor moving output for moving the self-propelled harmful agent detector; and wherein the sensor can measure levels of harmful agent concentration, and wherein the detector has a controller for propelling the detector toward areas having higher harmful agent concentrations.

17. A self-propelled harmful agent detector for traversing spaces in buildings comprising:

a harmful agent sensor for sensing chemical and/or biological agents injurious to human health, the harmful agent sensor having a data output;

a transmitter coupled to the harmful agent sensor data output for transmitting data from the self-propelled harmful agent detector;

a motor having a moving output; and a traction device coupled to the motor moving output for moving the self-propelled harmful agent detector; and wherein the detector has a receiver for receiving transmissions from other harmful agent detectors, and a relay for re-transmitting the received transmissions.

18. A self-propelled harmful agent detector for traversing spaces in buildings comprising:

a harmful agent sensor for sensing chemical and/or biological agents injurious to human health, the harmful agent sensor having a data output;

a transmitter coupled to the harmful agent sensor data output for transmitting data from the self-propelled harmful agent detector;

a power source;

a motor having a moving output and being supplied with power from the power source; and a traction device coupled to the motor moving output for moving the self-propelled harmful agent detector; and a controller for controlling the motor such that the self-propelled harmful agent detector is moved along one or more predefined paths;

further comprising a compartment for carrying equipment to building inhabitants.

19. A self-propelled harmful agent detector as in claim 18, further comprising safety equipment disposed within the compartment.

20. A self-propelled harmful agent detector as in claim 18, further comprising bi-directional communication equipment for communicating between people near the detector and people remote from the detector.

21. A system for monitoring harmful agents in buildings, the system comprising:

at least one self-propelled harmful agent detector for traversing spaces in buildings, the at least one self-propelled harmful agent detector including:

a harmful agent sensor for sensing chemical and/or biological agents injurious to human health, the harmful agent sensor having a data output;

a transceiver coupled to the harmful agent sensor data output for transmitting data from the self-propelled harmful agent detector and receiving instructions from a central control station;

a motor having a moving output;

a traction device coupled to the motor moving output for moving the self-propelled harmful agent detector; and a controller for controlling the motor such that the self-propelled harmful agent detector is moved along one or more predefined paths, the controller being coupled to the transceiver to receive instructions related to controlling the motor and the traction device, wherein the controller is adapted to modify a predefined path in response to instructions received by the transceiver;

a receiver for receiving the transmitted sensor data from the at least one self-propelled harmful agent detector; and a central control station for directing the at least one self-propelled harmful agent detector along one or more predefined paths in the building.

22. A system as in claim 21, wherein the self-propelled detector is self-powered.

23. A system as in claim 21, wherein the self-propelled detector sensor can measure levels of harmful agent concentration, wherein the sensor data contains data indicating harmful agent levels, wherein the transmitter can transmit the agent level data, and wherein the receiver can receive the transmitted agent level data.

24. A system for monitoring harmful agents in buildings the system comprising:
   at least one self-propelled harmful agent detector for traversing spaces in buildings, the at least one self-propelled harmful agent detector including:
      a harmful agent sensor for sensing chemical and/or biological agents injurious to human health, the harmful agent sensor having a data output;
      a transmitter coupled to the harmful agent sensor data output for transmitting data from the self-propelled harmful agent detector;
      a motor having a moving output; and
      a traction device coupled to the motor moving output for moving the self-propelled harmful agent detector;
   a receiver for receiving the transmitted sensor data from the at least one self-propelled harmful agent detector; and
   a controller for directing the at least one self-propelled harmful agent detector along one or more predefined paths in the building;
   wherein the self-propelled harmful agent detector can transmit an identification code identifying the identity of the device.

25. A system for monitoring harmful agents in buildings, the system comprising:
   at least one self-propelled harmful agent detector for traversing spaces in buildings, the at least one self-propelled harmful agent detector including:
      a harmful agent sensor for sensing chemical and/or biological agents injurious to human health, the harmful agent sensor having a data output;
      a transmitter coupled to the harmful agent sensor data output for transmitting data from the self-propelled harmful agent detector;
      a motor having a moving output; and
      a traction device coupled to the motor moving output for moving the self- propelled harmful agent detector;
   a receiving the transmitted sensor data from the at least one self-propelled harmful agent detector; and
   a controller for directing the at least one self-propelled harmful agent detector along one or more predefined paths in the building;
   wherein the self-propelled harmful agent detector has knowledge of its position and can transmit the position through the transmitter, wherein the receiver can receive and record the transmitted and received position.

26. A system as in claim 21, wherein the controller is coupled to the receiver for receiving the data.

27. A system for monitoring harmful agents in buildings, the system comprising:
   at least one self-propelled harmful agent detector for traversing spaces in buildings, the at least one self-propelled harmful agent detector including:
      a harmful agent sensor for sensing chemical and/or biological agents injurious to human health, the harmful agent sensor having a data output;
      a transmitter coupled to the harmful agent sensor data output for transmitting data from the self-propelled harmful agent detector;
      a motor having a moving output; and
      a traction device coupled to the motor moving output for moving the self-propelled harmful agent detector;
   a receiver for receiving the transmitted sensor data from the at least one self-propelled harmful agent detector; and
   a controller for directing the at least one self-propelled harmful agent detector along one or more predefined paths in the building;
   wherein the controller is coupled to the receiver for receiving the data; and the controller includes an executable program for analyzing the data.

28. A system as in claim 27, wherein the controller includes an executable program for at least partially controlling a building HVAC system and the controller is coupled to the HVAC system.

29. A system for monitoring harmful agents in buildings, the system compring:
   at least one self-propelled harmful agent detector for traversing spaces in buildings, the at least one self-propelled harmful agent detector including:
      a harmful agent sensor for sensing chemical and/or biological agents injurious to human health, the harmful agent sensor having a data output;
      a transmitter coupled to the harmful agent sensor data output for transmitting data from the self-propelled harmful agent detector;
      a motor having output; and
      a traction device coupled to the motor moving output for moving the self-propelled harmful agent detector;
   a receiver for receiving the transmitted sensor data from the at least one self-propelled harmful agent detector; and
   a controller for directing the at least one self-propelled harmful agent detector along one or more predefined paths in the building;
   wherein the receiver further has transmission capabilities, and the at least one self-propelled agent detector has reception capabilities, such that an operator at the receiver can communicate with people located near the self-propelled harmful agent detector.

30. A method for monitoring harmful agents in a building comprising:
   providing a system for monitoring harmful agents in the building, the system including at least one self-propelled harmful agent detector for traversing spaces in the building, the at least one self-propelled detector including:
      a harmful agent sensor for sensing chemical and/or biological agents injurious to human health, the harmful agent sensor having a data output;
      a transceiver coupled to the harmful agent sensor data output for transmitting data from the self-propelled harmful agent detector and adapted to receive information from a central control station;
      a motor having a moving output;
      a traction device coupled to the motor moving output for moving the self-propelled harmful agent detector; and
      a controller for controlling the motor such that the self-propelled harmful agent detector is moved along one or more predefined paths, the controller being coupled to the transceiver to receive instructions related to controlling the motor and the traction device, wherein the controller is adapted to modify a predefined path in response to instructions received by the transceiver;

providing a receiver for receiving the transmitted sensor data from the at least one self-propelled harmful agent detector; and disposing the at least one harmful agent detector within the building; and moving the at least one harmful agent detector throughout the building along one or more predefined paths and transmitting the harmful agent sensor data.

31. A method as in claim 30, wherein the self-propelled detector sensor can measure levels of harmful agent concentration, wherein the sensor data contains data indicating the harmful agent levels, wherein the transmitter can transmit the agent level data, and wherein the receiver can receive the transmitted agent level data, wherein the method further comprises receiving and storing the received harmful agent levels.

32. A method for monitoring harmful agents in a building comprising:

providing a system for monitoring harmful agents in the building, the system including at least one self-propelled harmful agent detector for traversing spaces in the building, the at least one self-propelled detector including:
 a harmful agent sensor for sensing chemical and/or biological agents injurious to human health, the harmful agent sensor having a data output;
 a transmitter coupled to the harmful agent sensor data output for transmitting data from the self-propelled harmful agent detector;
 a motor having a moving output; and
 a traction device coupled to the motor moving output for moving the self-propelled harmful agent detector;

providing a receiver for receiving the transmitted sensor data from the at least one self-propelled harmful agent detector; and disposing the at least one harmful agent detector within the building; and moving the at least one harmful agent detector throughout the building along one or more predefined paths and transmitting the harmful agent sensor data;

wherein the self-propelled harmful agent detector can transmit an identification code identifying the identity of the device, wherein the method further comprises receiving and mapping the identity of the harmful agent detectors.

33. A method for monitoring harmful agents in a building comprising:

providing a system for monitoring harmful agents in the building, the system including at least one self-propelled harmful agent detector for traversing spaces in the building, the at least one self-propelled detector including:
 a harmful agent sensor for sensing chemical and/or biological agents injurious to human health, the harmful agent sensor having a data output;
 a transmitter coupled to the harmful agent sensor data output for transmitting data from the self-propelled harmful agent detector;
 a motor having a moving output; and
 a traction device coupled to the motor moving output for moving the self-propelled harmful agent detector;

providing a receiver for receiving the transmitted sensor data from the at least one self-propelled harmful agent detector; and disposing the at least one harmful agent detector within the building; and moving the at least one harmful agent detector throughout the building along one or more predefined paths and transmitting the harmful agent sensor data;

wherein at least some of the self-propelled detectors are disposed within air ducts.

34. A method as in claim 30, wherein at least some of the self-propelled detectors are disposed on building floors.

35. A method for monitoring harmful agents in a building comprising:

providing a system for monitoring harmful agents in the building, the system including at least one self-propelled harmful agent detector for traversing spaces in the building, the at least one self-propelled detector including:
 a harmful agent sensor for sensing chemical and/or biological agents injurious to human health, the harmful agent sensor having a data output;
 a transmitter coupled to the harmful agent sensor data output for transmitting data from the self-propelled harmful agent detector;
 a motor having a moving output; and
 a traction device coupled to the motor moving output for moving the self-propelled harmful agent detector;

providing a receiver for receiving the transmitted sensor data from the at least one self-propelled harmful agent detector; and disposing the at least one harmful agent detector within the building; and moving the at least one harmful agent detector throughout the building along one or more predefined paths and transmitting the harmful agent sensor data;

wherein at least some of the self-propelled detectors are disposed in building elevator shafts.

36. A method for monitoring harmful agents in a building comprising:

providing a system for monitoring harmful agents in the building, the system including at least one self-propelled harmful agent detector for traversing spaces in the building, the at least one self-propelled detector including:
 a harmful agent sensor for sensing chemical and/or biological agents injurious to human health, the harmful agent sensor having a data output;
 a transmitter coupled to the harmful agent sensor data output for transmitting data from the self-propelled harmful agent detector;
 a motor having a moving output; and
 a traction device coupled to the motor moving output for moving the self-propelled harmful agent detector;

providing a receiver for receiving the transmitted sensor data from the at least one self-propelled harmful agent detector; and disposing the at least one harmful agent detector within the building; and moving the at least one harmful agent detector throughout the building along one or more predefined paths and transmitting the harmful agent sensor data;

wherein at least some of the self-propelled detectors are suspended on wires.

37. A method for monitoring harmful agents in a building comprising:
   providing a system for monitoring harmful agents in the building, the system including at least one self-propelled harmful agent detector for traversing spaces in the building, the at least one self-propelled detector including:
      a harmful agent sensor for sensing chemical and/or biological agents injurious to human health, the harmful agent sensor having a data output;
      a transmitter coupled to the harmful agent sensor data output for transmitting data from the self-propelled harmful agent detector;
      a motor having a moving output; and
      a traction device coupled to the motor moving output for moving the self-propelled harmful agent detector;
   providing a receiver for receiving the transmitted sensor data from the at least one self-propelled harmful agent detector; and
   disposing the at least one harmful agent detector within the building; and
   moving the at least one harmful agent detector throughout the building along one or more predefined paths and transmitting the harmful agent sensor data;
   wherein at least some of the self-propelled detectors are suspended on horizontal wires.

38. A method for monitoring harmful agents in a building comprising:
   providing a system for monitoring harmful agents in the building, the system including at least one self-propelled harmful agent detector for traversing spaces in the building, the at least one self-propelled detector including:
      a harmful agent sensor for sensing chemical and/or biological agents injurious to human health, the harmful agent sensor having a data output;
      a transmitter coupled to the harmful agent sensor data output for transmitting data from the self-propelled harmful agent detector;
      a motor having a moving output; and
      a traction device coupled to the motor moving output for moving the self-propelled harmful agent detector;
   providing a receiver for receiving the transmitted sensor data from the at least one self-propelled harmful agent detector; and
   disposing the at least one harmful agent detector within the building; and
   moving the at least one harmful agent detector throughout the building along one or more predefined paths and transmitting the harmful agent sensor data;
   wherein at least some of the self-propelled detectors are suspended on vertical wires.

39. A method for monitoring harmful agents in a building comprising:
   providing a system for monitoring harmful agents in the building, the system including at least one self-propelled harmful agent detector for traversing spaces in the building, the at least one self-propelled detector including:
      a harmful agent sensor for sensing chemical and/or biological agents injurious to human health, the harmful agent sensor having a data output;
      a transmitter coupled to the harmful agent sensor data output for transmitting data from the self-propelled harmful agent detector;
      a motor having a moving output; and
      a traction device coupled to the motor moving output for moving the self-propelled harmful agent detector;
   providing a receiver for receiving the transmitted sensor data from the at least one self-propelled harmful agent detector; and
   disposing the at least one harmful agent detector within the building; and
   moving the at least one harmful agent detector throughout the building along one or more predefined paths and transmitting the harmful agent sensor data;
   wherein at least some of the self-propelled detectors are disposed on a pendulum.

* * * * *